(12) United States Patent
Kapusta et al.

(10) Patent No.: US 9,642,566 B2
(45) Date of Patent: May 9, 2017

(54) FLEXIBLE EMBEDDED SENSOR ARRAYS AND METHODS OF MAKING THE SAME

(71) Applicant: General Electric Company, Schenectady, NY (US)

(72) Inventors: Christopher James Kapusta, Delanson, NY (US); Eric Patrick Davis, Niskayuna, NY (US); Jason Harris Karp, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 278 days.

(21) Appl. No.: 14/045,809

(22) Filed: Oct. 4, 2013

(65) Prior Publication Data

US 2015/0099948 A1 Apr. 9, 2015

(51) Int. Cl.
*G01L 1/04* (2006.01)
*A61B 5/1455* (2006.01)

(52) U.S. Cl.
CPC .... *A61B 5/14552* (2013.01); *A61B 2562/046* (2013.01); *A61B 2562/12* (2013.01); *Y10T 29/49004* (2015.01); *Y10T 29/49126* (2015.01)

(58) Field of Classification Search
CPC ............ A61B 5/14551; A61B 5/14552; A61B 5/6826; A61B 5/6838; A61B 5/1495
See application file for complete search history.

(56) References Cited

U.S. PATENT DOCUMENTS

| 5,263,244 | A | 11/1993 | Centa et al. |
| 5,797,767 | A | 8/1998 | Schell |
| 7,052,924 | B2 | 5/2006 | Daniels et al. |
| 7,830,470 | B2 | 11/2010 | Liu |
| 7,870,997 | B2 | 1/2011 | Eastman et al. |
| 7,952,107 | B2 | 5/2011 | Daniels et al. |
| 8,338,842 | B2 * | 12/2012 | Lerman ............... H01L 25/0753 257/100 |
| 8,461,602 | B2 * | 6/2013 | Lerman ............... H01L 25/0753 257/88 |
| 2003/0153108 | A1 * | 8/2003 | Durocher ................ H01L 23/13 438/26 |
| 2005/0212439 | A1 | 9/2005 | Zampini et al. |
| 2008/0225523 | A1 * | 9/2008 | De Samber ............... F21K 9/00 362/249.01 |
| 2012/0112235 | A1 | 5/2012 | Preuschl et al. |
| 2012/0244651 | A1 * | 9/2012 | Chen ..................... H01L 33/486 438/26 |

(Continued)

FOREIGN PATENT DOCUMENTS

| EP | 0510274 A1 * | 10/1992 | ................ B41J 2/45 |
| JP | H0734422 A | 2/1995 | |
| WO | 2012061183 A2 | 5/2012 | |

*Primary Examiner* — Tse Chen
*Assistant Examiner* — Yoojin Lee
(74) *Attorney, Agent, or Firm* — Melissa K. Dobson (57) ABSTRACT

A flexible embedded sensor array includes a first substrate, an electrically conductive pad disposed on at least a portion of the first substrate, and a plurality of sensors disposed on at least a portion of electrically conductive pads. Further, the flexible embedded sensor array includes an electrically non-conductive adhesive material disposed in proximity to one or more of the plurality of sensors, a second substrate, and an electrical contact disposed between at least a portion of the sensor and at least a portion of the second substrate.

12 Claims, 9 Drawing Sheets

(56) References Cited

U.S. PATENT DOCUMENTS

2012/0320532 A1 12/2012 Wang
2013/0213697 A1* 8/2013 Palaniswamy ........ H01L 33/486
                                                        174/254

* cited by examiner

FLEXIBLE EMBEDDED SENSOR ARRAYS AND METHODS OF MAKING THE SAME

This invention was made with Government support under grant number W81XWH-11-1-0833 POC awarded by the U.S. Army. The Government has certain rights in the invention.

BACKGROUND

Embodiments of the present disclosure relates to sensor arrays, and more particularly to flexible embedded sensor arrays.

Light emitting diodes are useful in a wide variety of applications. Typically, a light emitting diode array includes a plurality of diodes that are mounted on a common substrate. The light emitting diode arrays are used as light sources in an increasing variety of applications including healthcare, communications and instrumentation, commercial and household lighting, and automotive and visual displays. The light emitting diode arrays may include inorganic or organic light emitting diodes.

While lighting systems that employ arrays of light emitting diodes are desirable because of their low energy consumption, however, such systems are economically burdensome. For example, the inorganic light emitting diodes are usually bright and long lasting, however, the expenses incurred in manufacturing the inorganic light emitting diodes limit the use of the inorganic light emitting diodes in specific applications, such as billboard-size displays for sports arenas.

In addition to the monetary aspects, devices employing the arrays of the light emitting diodes face technical challenges. By way of example, such arrays include use of bonding techniques, such as wire bonding or soldering that result in a complex structure of the arrays. For example, in case of wire bonding, wirebonds having a length longer than a determined length may result in undesirable parasitic capacitance in the array. Typically, wire bonds may be substituted with solder bumps. Although the solder bumps are relatively smaller in size than the wire bonds, the solder bumps require high processing temperatures to form the bond. Moreover, the solder bumps also require different metallurgy on the bond pads that is not commonly available.

BRIEF DESCRIPTION

In one embodiment, a flexible embedded sensor array is provided. The flexible embedded sensor array includes a first substrate, a plurality of electrically conductive pads disposed on at least a portion of the first substrate, and a plurality of sensors disposed on corresponding electrically conductive pads of the plurality of electrically conductive pads. Further, the flexible embedded sensor array includes an electrically non-conductive adhesive material disposed in proximity to one or more of the plurality of sensors, a second substrate, and an electrical contact disposed between at least a portion of the plurality of sensors and at least a portion of the second substrate.

In another embodiment, a flexible embedded sensor array is provided. The flexible embedded sensor array includes a first substrate, a plurality of electrically conductive pads disposed on at least a portion of the first substrate, and a plurality of sensors disposed on corresponding electrically conductive pads of the plurality of electrically conductive pads. Further, the flexible embedded sensor array includes an electrically non-conductive adhesive material disposed in proximity to one or more of the plurality of sensors, a second substrate, and an electrical contact disposed between at least a portion of the plurality of sensors and at least a portion of the second substrate. Moreover, the flexible embedded sensor array includes a plurality of electrical routing; and surface mounted components.

In yet another embodiment, a method of making a flexible embedded sensor array includes providing a first substrate, providing a plurality of electrically conductive pads disposed on at least a portion of the first substrate, and disposing an electrically non-conductive adhesive material on at least a portion of the plurality of electrically conductive pads. Further, the method includes disposing a plurality of sensors on at least a portion of the plurality of electrically conductive pads having the electrically non-conductive adhesive material and applying a determined pressure on the plurality of sensors. Additionally, the method includes providing a second substrate, providing an electrical contact between at least a portion of one or more sensors of the plurality of sensors and at least a portion of the second substrate, and coupling a portion of the first substrate to the second substrate.

In another embodiment, a pulse oximetry system is provided. The pulse oximetry system includes a flexible embedded sensor array having emitters and an optical detector for detecting emission signals from the flexible embedded sensor array. Further, the pulse oximetry system includes a processor for processing the detected emission signals, and a display member configured to display data processed by the processor.

DRAWINGS

These and other features and aspects of embodiments of the invention will become better understood when the following detailed description is read with reference to the accompanying drawings in which like characters represent like parts throughout the drawings, wherein.

DETAILED DESCRIPTION

In certain embodiments of the present disclosure, flexible embedded sensor arrays and methods of making the same are provided. Advantageously, the flexible embedded sensor arrays may be bendable to a determined extent. Accordingly, the flexible embedded sensor arrays may be configured to be molded into non-flat shapes, as required, without producing undesirable strain in the arrays. In certain embodiments, the flexible embedded sensor arrays may be printed on one or more of flat, non-flat or flexible surfaces made of materials, such as, but not limited to, glass, plastic, rubber, or combinations thereof. The flexible embedded sensor arrays may be used in various applications, such as, but not limited to, general illumination, high-resolution home theater displays, wearable health monitors, and biomedical imaging devices.

Figure 1:
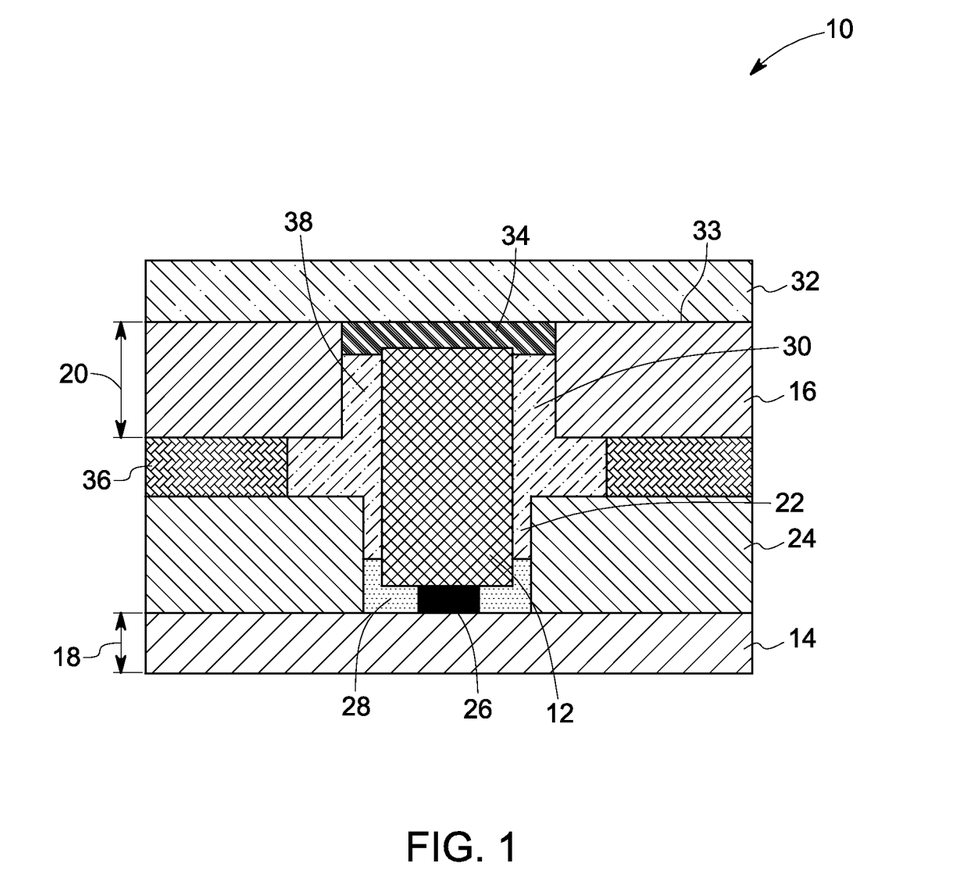
FIG. 1 is a cross-sectional view of a portion of an example flexible embedded sensor array, in accordance with aspects of the present disclosure.

FIG. 1 illustrates a cross-sectional view of a portion 10 of a flexible embedded sensor array (not shown) having a sensor 12 disposed between a first substrate 14 and a second substrate 16. Non-limiting examples of the sensor 12 may include transistors, emitters or detectors, or both. Non-limiting examples of the emitters and detectors may include diodes, light emitting diodes, photodiodes, transmitters, detectors, resistors, capacitors, amplifiers, transistors, individual integrated circuits (ICs), or combinations thereof. The light emitting diodes may include organic light emitting diodes, inorganic light emitting diodes, or both. The sensors of the flexible embedded sensor array may be part of a sensor drive or detection circuitry.

In some embodiments, the first substrate 14 may be a transmission substrate. In some of these embodiments, the first substrate 14 may be configured to allow at least a portion of emitted signal response from the sensor 12 to pass through the first substrate 14. By way of example, in case of the sensor 12 being a light emitting diode, the first substrate 14 may be configured to transmit at least a portion of light emitted by the sensor 12. Non-limiting examples of a material of the first substrate 14 may include polymer, rubber, glass, or combinations thereof. In one example, the first substrate 14 may be made of polyimide. A thickness 18 of the first substrate 14 may be selected so as to facilitate the flexibility of the array, while still providing mechanical stability and integrity to the array. In a non-limiting example, the thickness 18 of the first substrate 14 may be in a range from about 10 microns to about 50 microns. In a particular example, the thickness 18 of the first substrate 14 may be about 25 microns.

The portion 10 includes a cavity 22 defined by a first layer 24 disposed on the first substrate 14. The first layer 24 may be made of a polymer material. Non-limiting examples of the material for the first layer 24 may include polyimide. A part of the sensor 12 may be disposed in the cavity 22. In embodiments where the sensor 12 is a light emitting diode, the cavity 22 may be configured to guide radiation emitted from the light emitting diode towards the first substrate 14 and outside the portion 10 of the array. In some of these embodiments, the material of the first substrate 14 may be optically transparent to a wavelength of the light emitted by the light emitting diode. A size of the cavity 22 may be determined based on a size, structure and shape of the sensor 12. The sensor 12 may be disposed on an electrically conductive pad 26. The electrically conductive pad 26 may be configured to provide electrical contacts to the sensor 12. The electrically conductive pad 26 may be formed from a patterned layer having continuous or discontinuous portions of an electrically conductive material disposed on the first substrate 14. Non-limiting examples of the electrically conductive material suitable for the electrically conductive pad 26 may include gold, silver, titanium, copper, nickel, tin, aluminum, or combinations thereof.

The sensor 12 may be mechanically coupled to the first substrate 14 using an electrically non-conductive adhesive material 28. The non-conductive adhesive material 28 is configured to provide mechanical coupling between the first substrate 14 and the sensor 12. Further, using the non-conductive adhesive material 28 provides the mechanical coupling between the first substrate 14 and the sensor 12 while allowing an electrical contact between the electrically conductive pad 26 and the sensor 12. In one embodiment, the non-conductive adhesive material 28 is configured to form bonds upon exposure to determined environmental conditions, such as, but not limited to, a determined temperature, determined pressure, or both. In embodiments where the sensor 12 includes the light emitting diode, the non-conductive adhesive material 28 may be optically transparent to a wavelength of light emitted by the light emitting diode. Advantageously, use of the non-conductive adhesive circumvents any undesirable interference of the non-conductive adhesive with the bond pad metallurgy of the electrically conductive pad 26. As will be appreciated, the sensor 12 may be electrically coupled to the electrically conductive pad 26 using I/O contacts (not shown) of the sensor 12.

The second substrate 16 may be configured to provide a cavity 30 to house at least a portion of the sensor 12. A size of the cavity 30 may be determined based on a size of the sensor 12. The cavity 30 is provided to define a contact area between the sensor 12 and a layer 34 of an electrically conductive material. In one embodiment, the sensor 12 may be coupled to the electrically conductive material layer 34 using an electrically conductive epoxy. As will be appreciated, the sensor 12 may be electrically coupled to the layer 34 using I/O contacts (not shown) of the sensor 12. The second substrate 16 may be made of polymer, glass, rubber, or combinations thereof. In one example, the second substrate 16 may be made of polyimide. A thickness 20 of the second substrate 16 may be selected to facilitate the flexibility of the array while providing mechanical stability and integrity to the array. In a non-limiting example, the thickness 20 of the second substrate 16 may be in a range from about 10 microns to about 150 microns. In a particular example, the thickness 20 of the second substrate 16 may be in a range from about 25 microns to about 100 microns.

An electrical contact 32 may be disposed on a side 33 of the second substrate 16. The electrical contact 32 may be configured to provide electrical contact to a plurality of sensors (not shown) of the flexible embedded sensor array. Non-limiting examples of the electrical contact 32 may include copper, metal composites of copper, metal composites of copper and molybdenum, metal composites of copper and tungsten, composites of aluminum or copper graphite, copper clad metal alloys, or combinations thereof. In one example, metal alloys present in the copper clad metal alloys may include one or more of iron, nickel, cobalt or manganese (e.g., copper clad iron-nickel-cobalt alloy). The sensor 12 may be electrically coupled to the electrical contact 32 using the patterned electrically conductive layer 34. The electrical contact 32 may be configured to provide electrical coupling between the sensor 12 and an electrical device (not shown) or an electrical connection (not shown) that is external to the flexible embedded sensor array.

In one example, the plurality of sensors may share a common electrical contact. In this example, the common electrical contact may be in the form of a continuous or patterned layer. The common electrical contact may be common between a plurality of sensors of the sensor array.

The first layer 24 and the second substrate 16 may be mechanically coupled using a coupling medium 36. The coupling medium 36 may include one or more of an adhesive material, adhesive tape, mechanical fasteners, or combinations thereof. In some embodiments, the portion 10 may include a compliant medium 38 disposed between the first layer 24, the second layer 32, and the coupling medium 36. The compliant medium 38 may include fillers, such as but not limited to, epoxy filler. In one embodiment, the coupling medium 36 and compliant medium 38 may be made of same material.

Figure 2:
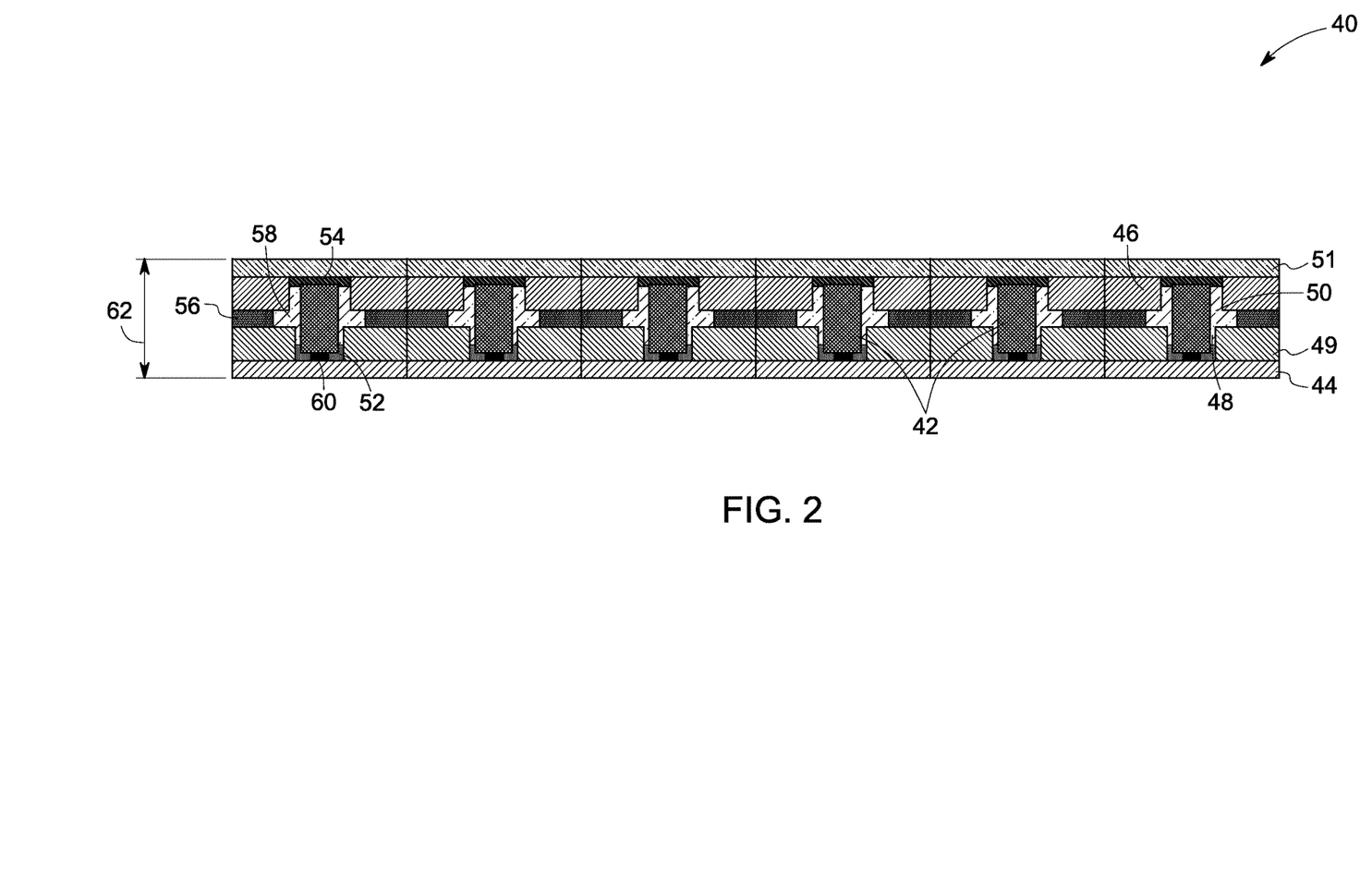
FIG. 2 is a cross-sectional view of an example flexible embedded sensor array, in accordance with aspects of the present disclosure.

FIG. 2 illustrates a cross-sectional view of an example flexible embedded sensor array 40 having a plurality of sensors 42. The plurality of sensors 42 may be substantially similar or different types. In one embodiment, some of the sensor 42 may be red wavelength emitting sensors, and other sensors 42 may be infrared wavelength emitting sensors. Non-limiting examples of the type of sensors may include light emitting diodes, transmitters, photodiodes, photodetectors, resistors, capacitors, amplifiers, transistors, individual circuits, or combinations thereof. The array 40 may include a first substrate 44 and a second substrate 46. The array 40 may further include a first layer 49 disposed on the first substrate 44 to define cavities 48 for disposing the sensors 42. Further, the array 40 may include a plurality of cavities 50. The cavities 50 may be defined by the second substrate 46 and an electrical contact 51. The array 40 may further include a plurality of portions of non-conductive adhesive 52 and a plurality of electrically conductive pads 60. The electrically conductive pads 60 are configured to act as flexible electrical circuit to provide individual electrical contact to the sensors 42. The sensors 42 may be individually and independently controlled using the flexible electrical circuit formed by electrically conductive layers 54 and the electrically conductive pads 60. As will be appreciated, the sensors 42 may be electrically coupled to the electrically conductive layers 54 and 60 using I/O contacts (not shown) of the sensors 42. The electrical contact 51 may be configured to provide electrical contact to the plurality of sensors 42 of the flexible embedded sensor array 40. Additionally, the array may include a coupling medium 56 and a compliant medium 58 disposed around the sensors 42. In one example, the coupling medium 56 and the compliant medium 58 may be made of same or similar material.

A size of the flexible array 40 may be decided based on the application. In one example, the flexible array 40 may include a 4×4 or 6×6 array of sensors. The sensor array 40 may be used in a vast range of applications, such as, but not limited to, indoor lightings, display lights, decorative lights, sign boards, detectors, diagnostic devices, healthcare systems, or combinations thereof. In certain embodiments, the flexible embedded sensor array 40 may be employed in detection sensors, such as but not limited to, a pulse oximeter. In certain other embodiments, the flexible embedded sensor array may be employed in display applications (display products, display sensors, or signage), light sensors, lighting sensors, or combinations thereof. Advantageously, the flexible sensor array 40 is thin, robust and flexible. The flexible embedded sensor array 40 may be thin enough to bend to a desirable extent without introducing any undesirable strains in the array 40. In one embodiment, a thickness 62 of the flexible sensor array 40 may be in a range from about 50 microns to about 500 microns. Also, in one example, the array 40 may be used to produce diffused and even lighting of one or more wavelengths.

Figure 3:
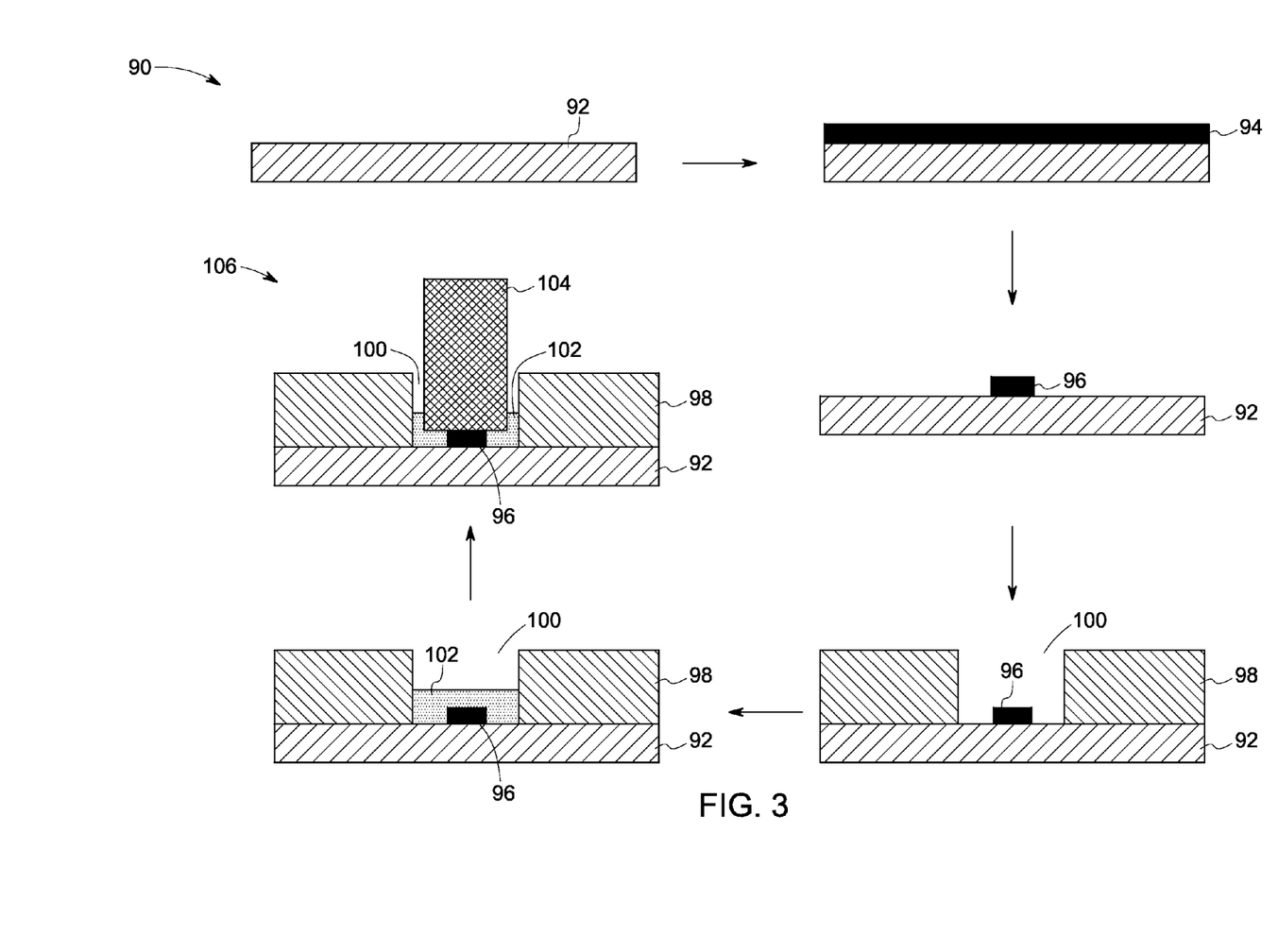
FIGS. 3-5 are cross-sectional views of an example method of making a flexible embedded sensor array, in accordance with aspects of the present disclosure.

FIG. 3 illustrates a portion of a flow diagram 90 of an example method of making at least a portion of a flexible embedded sensor array of the present disclosure. The method includes providing a first substrate 92. Non-limiting examples of the material of the first substrate 92 may include polyimide. In one example, the step of providing the first substrate 92 may include forming a film of the material of the first substrate 92. In another example, the step of providing the first substrate 92 may include providing a pre-fabricated or purchased film.

The method further includes providing a layer 94 disposed on at least a portion of the first substrate 92, where the layer 94 is made of an electrically conductive material suitable for electrically conductive pads. Next, the layer 94 may be patterned to form the electrically conductive pads 96 which act as flexible electrical circuits to provide electrical connection to sensors of the flexible embedded sensor array. In one embodiment, patterning the electrically conductive pads 96 may include masking and etching. In one example, the electrically conductive pads 96 and routing/interconnect (not shown) may be directly formed on the first substrate 92 instead of disposing the layer 94 and then patterning the layer 94. Non-limiting examples of techniques suitable for directly forming the pads 96 on the first substrate 92 may include film deposition methods or printing techniques. The techniques for forming the metal interconnect may include deposition techniques, such as, but not limited to, spray deposition, vapor deposition techniques, plasma assisted deposition techniques, or printing techniques. Non-limiting examples of the printing techniques may include techniques, such as, but not limited to, screen printing for flat surface, inkjet printing for flat surface, pad printing for curved surface, gravure printing, flexographic printing, conventional flex circuit fabrication, printed circuit board fabrication, or combinations thereof.

The method may further include disposing a first layer 98 on at least a portion of the first substrate 92 to define a cavity 100 for disposing a sensor. In one embodiment, the first layer 98 may be disposed as a continuous layer. Subsequently, the cavity 100 may be defined by removing a portion of the first layer 98. In one embodiment, the portion of the first layer 98 may be removed by etching, ablation (e.g., laser ablation, and the like). Although not illustrated, in an alternative embodiment, the first substrate 92 may be used to define the cavity 100. In this embodiment, the first layer 98 may not be required.

Additionally, the method may include disposing a layer 102 of a non-conductive adhesive material on at least a portion of the electrically conductive pads 96. In one embodiment, the non-conductive adhesive material may include an epoxy-based adhesive. In one embodiment, the non-conductive adhesive may be a one-part adhesive, or multi-component adhesive. In case of multi-component adhesive the adhesive may be supplied in two or more parts that are mixed before application of the adhesive. In one example, the non-conductive adhesive material 102 may be a two-component adhesive. By way of example, the two-component adhesive may be a solvent-thinned adhesive. The non-conductive adhesive may be a chemically resistant adhesive that is configured to be disposed as a thin layer. Further, the non-conductive adhesive may have a desirable viscosity to enable the adhesive to at least partially displace from the electrically conductive pads 96 to facilitate physical contact between at least a portion of a sensor 104 and the electrically conductive pads 96. In a non-limiting example, the adhesive may be room temperature cured, or ultraviolet (UV) light cured. The non-conductive adhesive may be easy to use and disposed on the first substrate 92 by deposition techniques such as, but not limited to, screen printing, spray deposition, pasting, machine, dispensing, jetting, machine dispensed, stamping, hand applying, or combinations thereof.

In certain embodiments, the method may include providing a sensor 104 to be disposed in the cavity 100. The sensor 104 may be disposed on at least a portion of the electrically conductive pads 96 having the non-conductive adhesive material 102. After disposing the sensor 104 in the cavity 100, a determined amount of pressure may be applied on the sensor 104 to at least partially displace the non-conductive adhesive material 102 from the electrically conductive pads 96 to facilitate physical contact between at least a portion of the sensor I/O pads and the electrically conductive pads 96 in an sub-assembly 106. In addition to applying the determined amount of pressure, the sub-assembly 106 may be subjected to a determined amount of temperature for a period of cure time to facilitate adhesion between the non-conductive adhesive material 102 and the sensor 104. In one embodiment, the determined pressure, determined temperature, cure time, or combinations thereof, may be decided based on chemical composition, viscosity, or both of the non-conductive adhesive material 102.

In some embodiments, the method may include in-situ monitoring of displacement of the non-conductive adhesive material 102 to assess electrical contact between the sensor 104 and the electrically conductive pad 96. In addition to or alternatively, the method may include in-process monitoring of displacement of the non-conductive adhesive material 102 to assess electrical contact between the sensor 104 and the electrically conductive pad 96. In one embodiment, in-situ monitoring, in-process monitoring, or both, may be performed by monitoring a change in resistance or ohmic contact between the sensor 104 and the electrically conductive pad 96.

Figure 4:
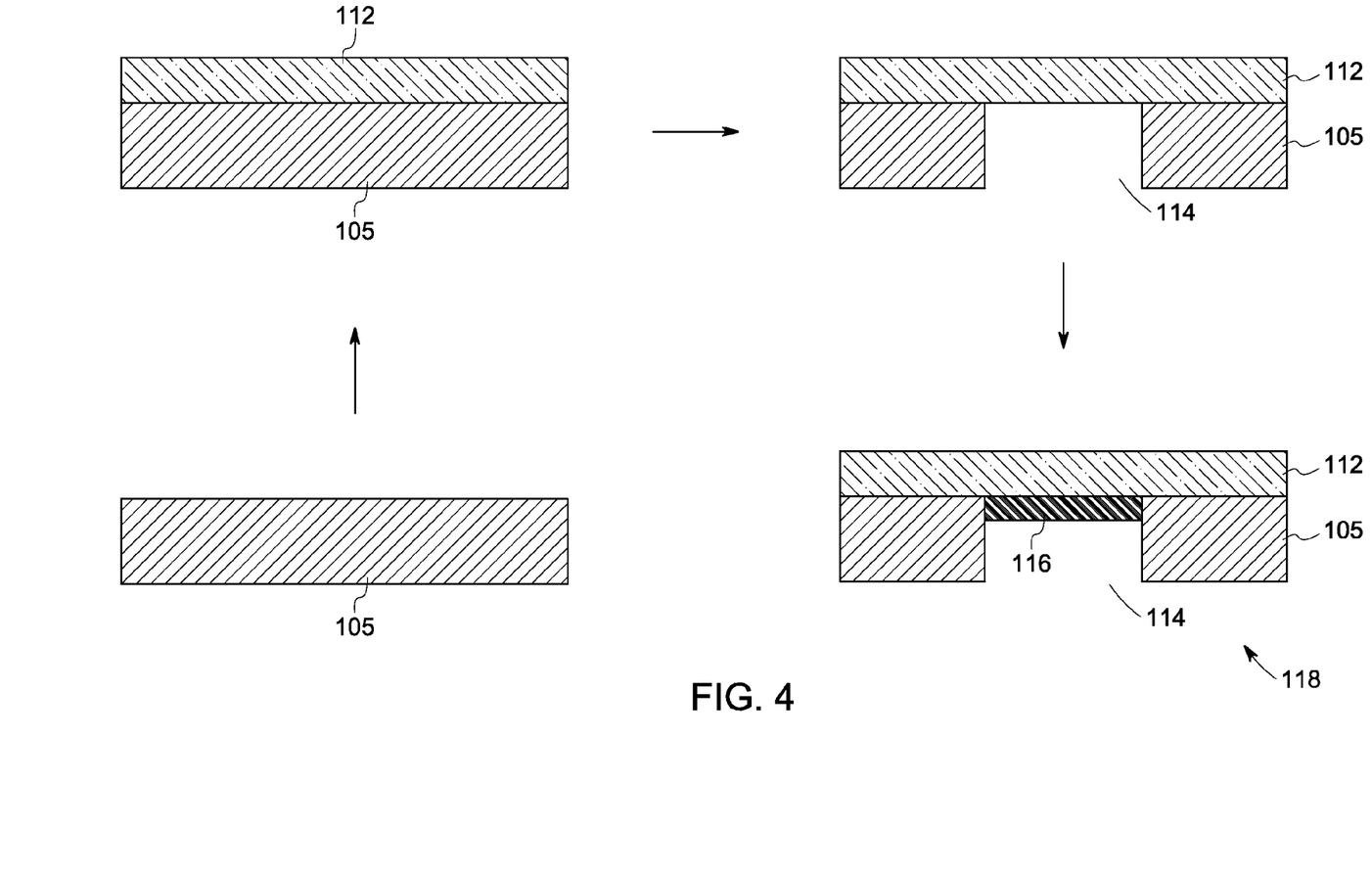

As illustrated in FIG. 4, the method may also include providing a second substrate 105. At least a portion of the second substrate 105 is patterned to define a cavity 114. In one embodiment, the patterning of the second substrate 105 may include etching, ablation (e.g., laser ablation), or both, to remove a portion of the second substrate 105 to define the cavity 114. The cavity 114 may be configured to receive at least a portion of the sensor 104 (see FIG. 3). An electrical contact layer 112 is disposed on a side of the second substrate 105. A layer 116 of an electrically conductive material may be disposed in at least a portion of the cavity 114 to form a sub-assembly 118. The electrically conductive material layer 116 may be in direct physical contact with the contact layer 112 to provide an electrical contact to the sensor 104. The second substrate 105 may be configured to provide mechanical integrity to the sensor array. As will be appreciated the sensor 104 may be electrically conductive to the electrically conductive pads 96 and layer 116 of the electrically conductive material using I/O contacts (not shown) of the sensor 104.

Figure 5:
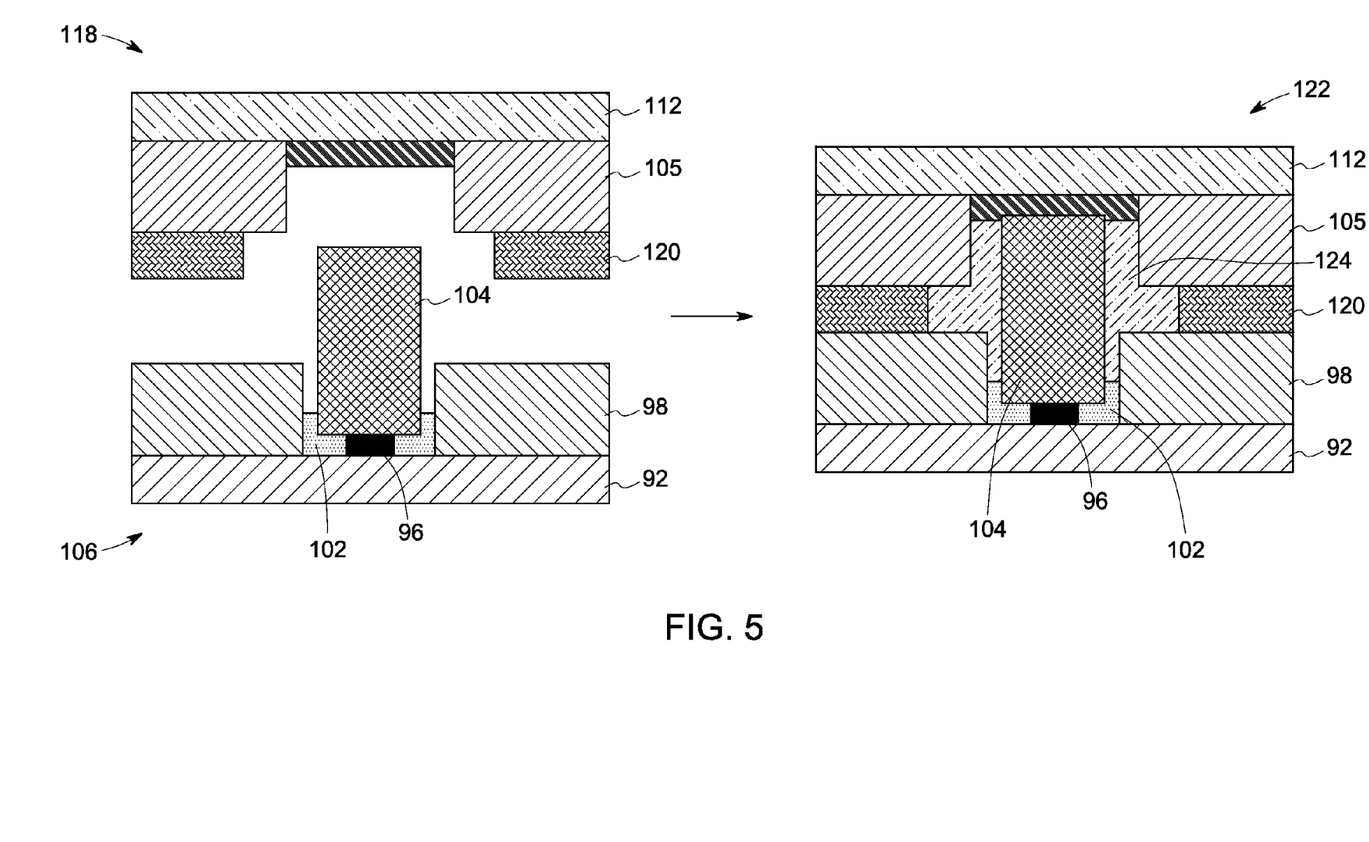

As illustrated in FIG. 5, sub-assemblies 106 and 118 may be aligned with respect to each other. Further, a coupling medium 120 may be disposed between the sub-assemblies 106 and 118 to couple the two sub-assemblies 106 and 118 together to form a portion 122 of a flexible embedded sensor array. Further, a compliant medium compliant medium 124 may be disposed between the two sub-assemblies 106 and 118. The compliant medium 124 may include fillers, such as but not limited to, epoxy filler. In one embodiment, the coupling medium 120 and compliant medium 124 may be made of same material. In some embodiments, the sub-assemblies 106 and 118 may be fabricated parallel in time. Fabricating the sub-assemblies 106 and 118 may reduce the manufacturing time, thereby making the process time efficient.

Figure 6:
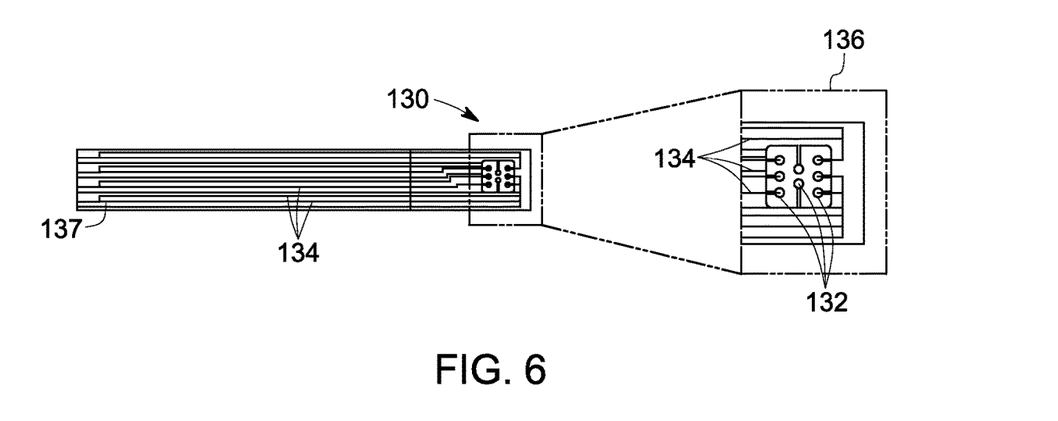
FIG. 6 is a top view of a portion of a flexible embedded sensor array having 8 light emitting diodes, where the flexible embedded sensor array is made using the method of the present disclosure.

FIG. 6 illustrates an example of a flexible embedded sensor array 130 made using the example method described in FIGS. 3-5. In the illustrated embodiment, the flexible embedded sensor array 130 includes an array of 8 individual light emitting diodes 132. Reference numeral 136 represents enlarged view of the array 130 of the light emitting diodes 132. Each individual light emitting diode 132 has a corresponding individual electrical connection 134 connected from the electrically conductive layer (not shown) of that particular light emitting diode 132 to an external electrical circuit 137. Each individual light emitting diode 132 may be controlled individually using the corresponding electrical connection 134.

Figure 7:
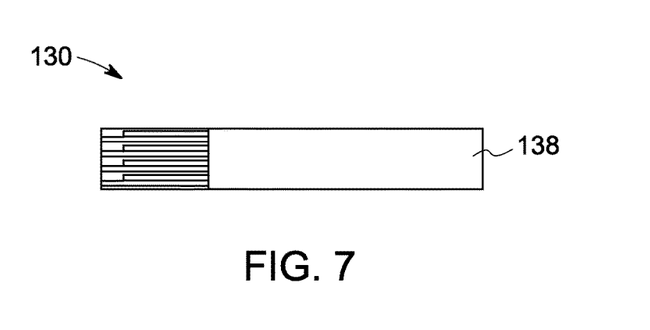
FIG. 7 is a back-side view of the flexible embedded sensor array of FIG. 6.

FIG. 7 illustrates a back-side view of the flexible embedded sensor array 130 of FIG. 6. As illustrated, an electrical contact 138 is disposed on the sensor array 130. The electrical contact 138 may be configured to provide a common electrical contact to the light emitting diodes 132. Further, the electrical contact 138 is configured to act as a thermal plane for at least a portion of the light emitting diodes 132 to enhance thermal dissipation of the heat generated in the array 130.

Figure 8:
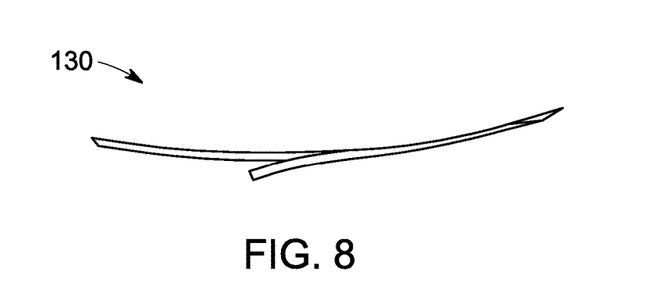
FIG. 8 is a side view of the flexible embedded sensor array of FIG. 6.

FIG. 8 illustrates a side view of the flexible embedded sensor array 130 of FIG. 6. As illustrated, the flexible embedded sensor array 130 has a thin and flexible structure. The thin and flexible structure of the flexible embedded sensor array 130 facilitates application of the sensor array 130 in various applications, such as, but not limited to, diagnostics, monitoring, sensing, or combinations thereof. The sensor array 130 may be printed or made using thin film processing steps on flat or flexible first and/or substrates. The sensor 130 may be made using roll-to-roll processing.

Figure 9:
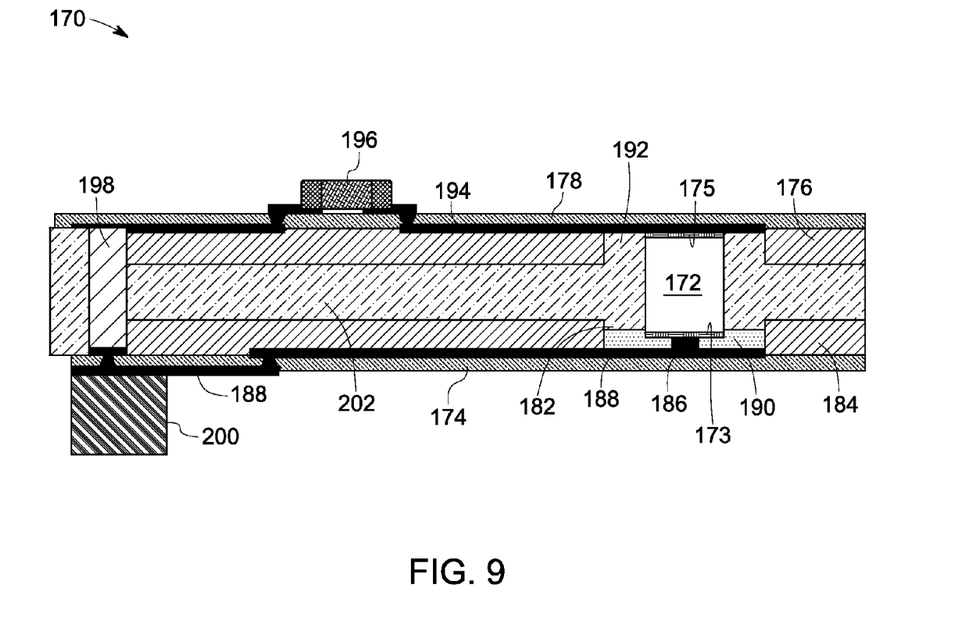
FIG. 9 is a cross-sectional view of a portion of a flexible embedded sensor array having connectors and surface mounted components, where the flexible embedded sensor array is made using the method of the present disclosure.

FIG. 9 illustrates a cross-sectional view of a portion 170 of a flexible embedded sensor array having a sensor 172 disposed between a first substrate 174 and a second substrate 176. The sensor 172 may be part of a sensor drive or detection circuitry. The portion 170 includes a cavity 182 defined by a first layer 184 disposed on the first substrate 174. Further, the sensor 172 may be disposed on an electrically conductive pad 186 configured to provide electrical contact to the sensor 172 via the first electrical routing 188. In one embodiment, the first electrical routing 188 may be disposed on a flex circuit having the electrically conductive pad 186. The sensor 172 may be mechanically coupled to the first substrate 174 using an electrically non-conductive adhesive material 190.

Moreover, the second substrate 176 may be configured to provide a cavity 192 to house at least a portion of the sensor 172. The cavity 192 is provided to define a contact area between the sensor 172 and a second electrical routing 194. The sensor 172 may include I/O contacts 173 and 175. The I/O contacts 173 and 175 are used to electrically couple the sensor 172 to the electrically conductive pad 186 and the second electrical routing 194, respectively. Further, the portion 170 may also include a backside substrate 178. Moreover, the portion 170 may include a surface mounted component 196, such as, but not limited to, a resistor, a capacitor, or both. Moreover, the portion 170 may include a through via 198 connected to an external device using an electrical connector 200. The electrical connector 200 may be configured to provide an electrical coupling between the sensor 172 and an electrical device (not shown) or an electrical connection (not shown) that is external to the flexible sensor array 170. The portion 170 may further include a compliant medium 202, such as, but not limited to, epoxy fillers. In a non-limiting example, the through via 198 may be filled with an electrically conductive material, such as, but not limited to, a metal slug.

Figure 10:
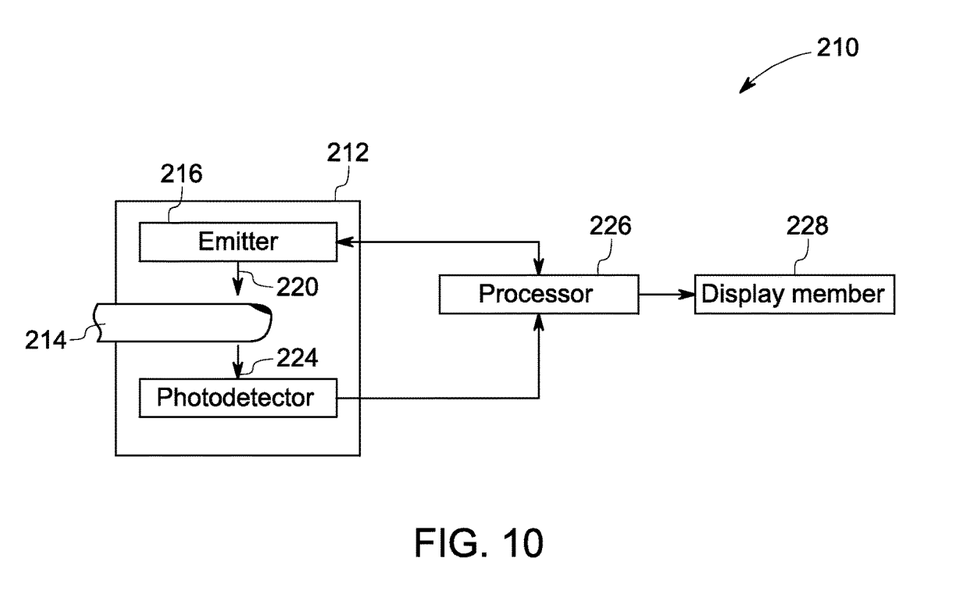
FIG. 10 is a block diagram of an example pulse oximetry system employing a flexible embedded sensor array of the present disclosure, in accordance with aspects of the present disclosure.

FIG. 10 illustrates an example embodiment of a pulse oximeter system 210 employing a pulse oximeter device 212. The pulse oximeter device 212 may be configured to be coupled to a patient. By way of example, the pulse oximeter device 212 may be configured to be coupled to a fingertip 214 of the patient. Alternatively, the pulse oximeter device 212 may be configured to be coupled to an earlobe, or in the case of an infant, a foot of the patient 214. The pulse oximeter device 212 may include an emitter 216 and a photodetector 224. The emitter 216 may include an array of light emitting diodes (not shown). The array of light emitting diodes may be a flexible embedded array of the present disclosure. The emitter 216 may be configured to emit light of two or more wavelengths. The emitted light 220 is passed through the patient, e.g., the fingertip 214. A portion of the light 220 passed through the fingertip 214 is absorbed or reflected by the tissues in the fingertip 214 and the remaining portion 222 may be received by a photodetector 224. The changing absorbance at each of the wavelengths from the emitter 216 may be measured using the photodetector 224. Based on the wavelengths measured at the different wavelengths absorbance due to the pulsing arterial blood alone may be determined using a processor 226. The absorbance due to arterial blood may exclude absorbance of light due to venous blood, skin, bone, muscle, fat, and other elements, such as nail paint. In one embodiment, based on the absorbance of light by the patient, the processor 226 may be configured to control wavelengths emitted by the emitter 216.

The system 210 may further include a display member 228 configured to display a blood saturation level. In one embodiment, the display member 228 may be integral part of the pulse oximeter device 212. Alternatively, the display member 228 may be external to the pulse oximeter device 212.

Figure 11:
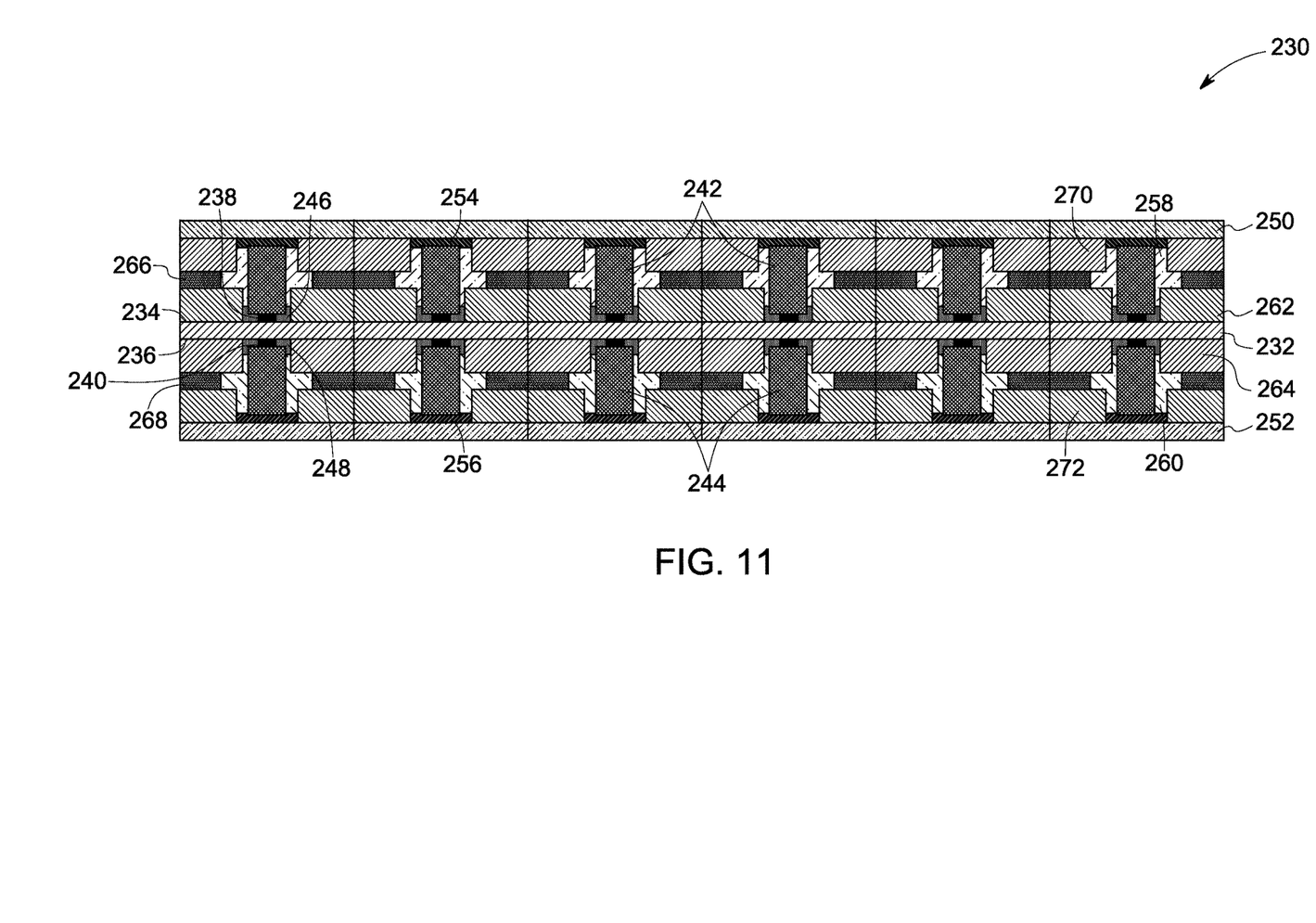
FIG. 11 is a block diagram of an example multilayers structure of a flexible embedded sensor array, in accordance with aspects of the present disclosure.

FIG. 11 illustrates an example of a multilayered flexible embedded sensor array 230 of the present disclosure. In the illustrated embodiment, the array 230 includes a first substrate 232 having a first side 234 and a second side 236. A first plurality of electrically conductive pads 238 are disposed on the first side 234 of the first substrate 232, a second plurality of electrically conductive pads 240 disposed on the second side 236 of the first substrate 232. The multilayered flexible embedded sensor array 230 further includes a first plurality of sensors 242 disposed on the first plurality of electrically conductive pads 238, and a second plurality of sensors 244 disposed on the second plurality of electrically conductive pads 240. Additionally, the multilayered flexible embedded sensor array 230 includes a first electrically non-conductive adhesive material 246 disposed in proximity to the first plurality of sensors 242, and a second electrically non-conductive adhesive material 248 disposed in proximity to the second plurality of sensors 244.

Moreover, the multilayered flexible embedded sensor array 230 includes a first backside substrate 250 and a second backside substrate 252. A first electrical contact 254 is disposed between the first plurality of sensors 242 and the first backside substrate 250. Similarly, a second electrical contact 256 is disposed between the second plurality of sensors 244 and the second backside substrate 252. The flexible embedded sensor array 230 further includes a first layer 262 disposed on the first side 234 of the first substrate 232, and another first layer 264 disposed on the second side 236 of the first substrate. The array further includes coupling media 266 and 268, and compliant media 258 and 260. In one embodiment, the coupling media 266 and 268, and the compliant media 258 and 260 may be made of same material. The array 230 may further include second substrate 270 and 272. Although not illustrated, the sensor array 230 may include surface mounted components, and electrical routing to facilitate electrical coupling between components of the sensor and external devices.

Advantageously, the flexible embedded sensor array may be formed on flat and non-flat surfaces with similar ease. Further, the method provides provisions for simultaneously performing one or more steps for different portions of the device substrate. The flexible embedded sensor arrays provide a thin and flexible structure which may be employed in various applications. The thin and flexible embedded sensor arrays may be printed for applications such as healthcare, lighting, monitoring, or combinations thereof. Advantageously, the flexible embedded sensor arrays and methods of making the same eliminate the need for wire-bonding of the sensor devices. As will be appreciated, wire-bonding may not be recommended for delicate devices, such as, sensor devices. Replacing individual wire-bonds with a laminated, patterned contact enables electrically coupling the sensor array and a plurality of devices using a single process step. By way of example, using the flexible electrically conductive pads and a common electrical contact enables electrical coupling between the sensor array to a plurality of devices in a single process step. The flexible embedded sensor arrays and methods of making the same also eliminate the need for high temperature processes, such as, but not limited to, solder attach processes. The flexible embedded sensor arrays provide a thin and flexible structure which may be employed in various applications. The thin and flexible embedded sensor arrays may be printed for applications such as healthcare, lighting, monitoring, or combinations thereof.

While only certain features of the invention have been illustrated and described herein, many modifications and changes will occur to those skilled in the art. It is, therefore, to be understood that the appended claims are intended to cover all such modifications and changes as fall within the scope of the invention.

The invention claimed is:
1. A flexible embedded sensor array, comprising:
a first substrate for allowing transmission from a plurality of sensors;
a plurality of electrically conductive pads disposed on at least a portion of the first substrate, wherein each sensor from the plurality of sensors is disposed on a corresponding electrically conductive pad from the plurality of electrically conductive pads, such that only a portion of each sensor is in contact with the corresponding electrically conductive pad;
an electrically non-conductive adhesive material disposed on the first substrate and in proximity to one or more of the plurality of sensors, and further in proximity to the portion of each sensor that is in contact with the corresponding electrically conductive pad;
a second substrate disposed at a distance from the first substrate, such that each of the plurality of sensors is disposed in a cavity defined by the first substrate and the second substrate;
an electrically conductive material layer disposed in the cavity on a front side of the second substrate; and an electrical contact disposed on a back side of the second substrate to provide electrical contact to the plurality of sensors through the electrically conductive material layer, wherein each sensor is controlled through an electrical connection provided by the corresponding electrically conductive pad.

2. The flexible embedded sensor array of claim 1, wherein the flexible embedded sensor array is configured to bend.

3. The flexible embedded sensor array of claim 1, wherein the first substrate, the second substrate, or both the first and second substrates comprise a film.

4. The flexible embedded sensor array of claim 1, wherein the plurality of electrically conductive pads comprises flexible circuits.

5. The flexible embedded sensor array of claim 1, wherein the first substrate is a transmission substrate for allowing at least a portion of emitted signal response from one or more sensors of the plurality of sensors to pass through the first substrate, and wherein a material of the first substrate is optically transparent to a wavelength of light emitted by the plurality of sensors.

6. The flexible embedded sensor array of claim 1, wherein the plurality of sensors comprises emitters, detectors, or both emitters and detectors.

7. The flexible embedded sensor array of claim 1, wherein the plurality of sensors comprises light emitting diodes, transmitters, photodiodes, photodetectors, resistors, capacitors, amplifiers, transistors, individual integrated circuits, or combinations thereof.

8. The flexible embedded sensor array of claim 1, wherein the electrically non-conductive adhesive is configured to form bonds upon exposure to a determined temperature, a determined pressure, or both determined temperature and determined pressure.

9. The flexible embedded sensor array of claim 1, further comprising a first layer disposed on the first substrate to define a cavity on the first substrate for each of the plurality of sensors, and wherein the cavity on the front side of the second substrate defines a contact area between a portion of each of the plurality of sensors and the electrically conductive material layer.

10. The flexible embedded sensor array of claim 1, wherein the electrically conductive layer is configured to electrically couple each sensor in the plurality of sensors to the electrical contact.

11. The flexible embedded sensor array of claim 1, wherein the electrical contact is a common electrical contact between two or more of the plurality of sensors.

12. The flexible embedded sensor array of claim 1, wherein the electrical contact acts as a thermal plane for at least a portion of the plurality of sensors.

* * * * *